US012746088B2

(12) United States Patent
Mannan

(10) Patent No.: US 12,746,088 B2
(45) Date of Patent: Sep. 29, 2026

(54) PHOTOTHERAPY SHIELD

(71) Applicant: University of Massachusetts, Boston, MA (US)

(72) Inventor: Javed Mannan, North Billerica, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 623 days.

(21) Appl. No.: 17/452,958

(22) Filed: Oct. 29, 2021

(65) Prior Publication Data

US 2023/0136463 A1 May 4, 2023

(51) Int. Cl.
*A61B 90/00* (2016.01)
*A61N 5/06* (2006.01)

(52) U.S. Cl.
CPC ............ *A61B 90/04* (2016.02); *A61N 5/0621* (2013.01); *A61B 2090/0454* (2016.02); *A61B 2090/049* (2016.02); *A61N 2005/0663* (2013.01)

(58) Field of Classification Search
CPC .... A61B 2090/0409; A61B 2090/0436; A61B 2090/0454; A61B 2090/049; A61B 90/04; A61B 46/00–40; A61N 2005/1094; A61N 2005/1097; A61N 2005/0663; A61N 5/062; A61N 5/0621; A61N 2005/064;
(Continued)

(56) References Cited

U.S. PATENT DOCUMENTS 4,604,998 A * 8/1986 Bellina .................. A61B 46/00
128/207.14
4,715,366 A * 12/1987 Teeple .................. A61B 90/04
606/2
(Continued)

FOREIGN PATENT DOCUMENTS

DE 69019971 T2 2/1995
WO 2023076987 A1 5/2023

OTHER PUBLICATIONS

Abdulla, F. R. et al., "Standards for genital protection in phototherapy units," J. Am. Acad. Dermatol., 62(2): 223-226 (2010).
(Continued)

*Primary Examiner* — Alireza Nia
*Assistant Examiner* — Robin Han
(74) *Attorney, Agent, or Firm* — Hamilton, Brook, Smith & Reynolds, P.C.

(57) ABSTRACT

A phototherapy shield for an infant includes a shield body that is sized and shaped to extend around at least a portion of a torso of an infant. The shield body includes a reflective foil layer that is sandwiched between an upper fabric layer and a lower fabric layer and that is configured to block phototherapy light. A fastener is attached to the shield body to secure the phototherapy shield around the infant's torso. The disclosed phototherapy shield and associated methods are useful for shielding an infant undergoing phototherapy, and more particularly, for shielding the chest of a premature infant undergoing phototherapy to treat jaundice. The shield body can be sized and shaped to cover the infant's chest over the second to fourth thoracic rib position to shield an area of skin above a patent ductus arteriosus (PDA).

16 Claims, 11 Drawing Sheets

(58) Field of Classification Search
CPC .... A61N 2005/0641; A61N 2005/0645; A61N 2005/0636; A61N 2005/0637; A61N 2005/0652; A61N 2005/0621; A61N 2005/0635; A61N 2005/0662; A61N 2005/0651; A61N 5/00; A61N 5/025; A41D 13/04; A41B 13/00; A41B 13/005; A41B 13/04; A41B 13/06; A41B 13/065; A41B 13/08; A41B 13/10; A41B 13/103; B32B 15/14; B32B 15/00; B32B 15/20; A61F 9/022
USPC .................................................. 128/846, 849
See application file for complete search history.

(56) References Cited

U.S. PATENT DOCUMENTS

| | | | | | |
|---|---|---|---|---|---|
| 4,735,623 | A * | 4/1988 | Hatzenbuhler | A61B 90/04 | 128/846 |
| 4,901,738 | A * | 2/1990 | Brink | B32B 15/14 | 606/2 |
| 5,219,650 | A * | 6/1993 | Ritter | B32B 27/12 | 428/323 |
| 5,336,248 | A | 8/1994 | Good et al. | | |
| 5,406,964 | A * | 4/1995 | Calleja | A61F 13/148 | 602/53 |
| 5,469,864 | A * | 11/1995 | Rosenblatt | A61B 90/04 | 128/207.14 |
| 6,973,930 | B2 * | 12/2005 | Chilton | A61F 9/04 | 128/858 |
| 11,020,610 | B2 | 6/2021 | Brezinski et al. | | |
| 2004/0138726 | A1 * | 7/2004 | Savage, Jr. | A61N 5/0621 | 607/88 |
| 2008/0116401 | A1 * | 5/2008 | Rice | A61N 5/0621 | 250/516.1 |
| 2018/0085249 | A1 * | 3/2018 | Carrasco | A61B 46/23 | |

OTHER PUBLICATIONS

Bashkatov, A.N. et al., "Optical properties of human skin, subcutaneous and mucous tissues in the wavelength range from 400 to 2000 nm," Journal of Physics D: Applied Physics, 38: 2543-2555 (2005).
Chin, K.C. et al., "Light transmission of phototherapy eyeshields," Archives of Disease in Childhood, 62: 970-971 (1987).
Crabb, M. et al., "Intense pulsed light therapy (IPL) induced iritis following treatment for a medial canthal capillary malformation," Australiasian Journal of Dermatology, 55: 289-291 (2014), doi: 10.1111/ajd.12137.
Csoma, Z. et al., "Neonatal Blue Light Phototherapy and Melanocytic Nevi: A Twin Study," Pediatrics, 128(4): e856-e864 (2011).
Dennis, J.E. et al., "Numerical Methods for Unconstrained Optimization and Nonlinear Equations," Classics in Applied Mathematics, 16, Prentice-Hall, Inc. Ed., Englewood Cliffs, NJ (1983).
Henyey, L.G. et al., "Diffuse radiation in the Galaxy," The Astrophysical Journal, 93: 70-83 (1941).
Holme, S.A., et al., "Phototherapy and PUVA photochemotherapy in children," Photodermatology Photoimmunology & Photomedicine, 20: 69-75 (2004).
Jacques, S.L. et al., "Thermally Induced Changes in Optical Properties of Heart," Images of the Twenty-First Century. Proceedings of the Annual International Engineering in Medicine and Biology Society, 4: 1199-1200 (1989), doi: 10.1109/IEMBS.1989.96158.
Javey, G. et al., "Ocular Complication of Intense Pulsed Light Therapy: Iris Photoablation," Dermatol Surg. 36: 1446-1468 (2010), doi: 10.1111/j.1524-4725.2010.01661.x.
Komericki, P. et al., "Keratopathy after ultraviolet B phototherapy," The Middle European Journal of Medicine, 117(7-8): 300-302 (2005).
Otman, S.G.H. et al., "Eye protection for ultraviolet B phototherapy and psoralen ultraviolet A patients," Photodermatology, Photoimmunology & Photomedicine, 26: 143-150 (2010).
Robinson, J. et al., "Light transmission measurements and phototherapy eyepatches," Archives of Disease in Childhood, 66: 59-61 (1991).
Salomatina, E. et al., "Optical properties of normal and cancerous human skin in the visible and near-infrared spectral range," Journal of Biomedical Optics, 11(6): 064026 (2006), https://doi.org/10.1117/1.2398928.
Skinner, M.G. et al., "Changes in optical properties of ex vivo rat prostate due to heating," Phys. Med. Biol., 45: 1375-1386 (2000).
Stokowski, L.A., "Fundamentals of Phototherapy for Neonatal Jaundice," Advances in Neonatal Care, 11(5S): S10-S21 (2011).
Yaroslavsky, A.N. et al., "Optical properties of selected native and coagulated human brain tissues in vitro in the visible and near infrared spectral range," Phys. Med. Biol., 47: 2059-2073 (2002).
Yaroslavsky, I.V. et al., "Inverse hybrid technique for determining the optical properties of turbid media from integrating-sphere measurements," Appl. Opt. 35(34): 6797-6809 (1996).
Benitz, W.E., "Treatment of persistent patent ductus arteriosus in preterm infants: time to accept the null hypothesis?" Journal of Perinatology, 30: 241-252 (2010).
Clyman, R.I., "Ibuprofen and Patent Ductus Arteriosus," The New England Journal of Medicine, 343: 728-730 (2000).
Clyman, R.I. et al., "Patent Ductus Arteriosus: A New Light on an Old Problem," Pediatric Res., 12: 92-94 (1978).
Foster, B.K., "Chest shielding for prevention of a haemodynamically significant patent ductus arteriosus in preterm infants receiving phototherapy (Review)," Cochrane Database of Systematic Reviews, Issue: 11, Art. No. CD009816, 25 pages (2015).
Furchgott, R.F., "Endothelium-Dependent Relaxation, Endothelium-Derived Relaxing Factor and Photorelaxation of Blood Vessels," Seminars in Perinatology, vol. 15, No. 1: 11-15 (Feb. 1991).
Furchgott, R.F., "Endothelium-Derived Relaxation Factor: Discovery, Early Studies, and Identification as Nitric Oxide," Bioscience Reports, vol. 19, No. 4: 235-251 (1998).
Furchgott, R.F., "The Discovery of Endothelium-Derived Relaxing Factor and Its Importance in the Identification of Nitric Oxide," The Journal of the American Medical Association, No. 276, No. 14, 1186-1188 (1996).
Furchgott, R.F. et al., "The Photoactivated Relaxation of Smooth Muscle of Rabbit Aorta," The Journal of General Physiology, vol. 44, pp. 499-519 (1961).
Herrman, K. et al., "Spontaneous closure of the patent ductus arteriosus in very low birth weight infants following discharge from the neonatal unit," Arch. Dis. Child Fetal Neonatal. Ed., 94: F48-F50 (2009).
Hoffman, J.I.E. et al., "The Incidence of Congenital Heart Disease," Journal of the American College of Cardiology, vol. 39, No. 12, pp. 1890-1900 (2002).
Kapoor, S. et al., "Chest shielding in preterm neonates under phototherapy—a randomised control trial," European Journal of Pediatrics, 180: 767-773 (2021).
Kim, H.S. et al., "Influence of Phototherapy on Incidence of Patent Ductus Arteriosus in Very Low Birth Weight Infants," vol. 40, No. 10, pp. 1411-1417 (1997) (English Language Abstract Attached).
Koch, J. et al., "Prevalence of Spontaneous Closure of the Ductus Arteriosus in Neonates at a Birth Weight of 1000 Grams or Less," Pediatrics, vol. 11, No. 4: 1113-1121 (2006).
Mannan, J. et al., "Meta-Analysis of the Effect of Chest Shielding on Preventing Patent Ductus Arteriosus in Premature Infants," Am. J. Perinatol., 34: 359-363 (2017).
Muraskas, J. et al., "The Cost of Saving the Tiniest Lives: NICUs versus Prevention," American Medical Association Journal of Ethics, vol. 10, No. 10: 655-658 (2008).
Richards, J. et al., "A Second Course of Ibuprofen Is Effective in the Closure of a Clinically Significant PDA in ELBW Infants," Pediatrics, vol. 124, No. 2: e287-e293 (2009).
Sallmon, H. et al., "Recent Advances in the Treatment of Preterm Newborn Infants with Patent Ductus Arteriosus," Clin. Perinatol., 43: 113-129 (2016).

(56) References Cited

OTHER PUBLICATIONS

Schneider, D.J. et al., “Congenital Heart Disease for the Adult Cardiologist: Patent Ductus Arteriosus,” Circulation, 114: 1873-1882 (2006).
Skinner, J., “Diagnosis of patent ductus arteriosus,” Semin. Neonatal., 6: 49-61 (2001).
The Investigators of the Vermont-Oxford Trials Network Database Project, “The Vermont-Oxford Trials Network: Very Low Birth Weight Outcomes for 1990,” Pediatrics, vol. 91, No. 3 (Mar. 1993).
Barefield et al., “Association of patent ductus arteriosus and phototherapy in infants weighing less than 1000 grams,” J Perinatol, 13: 376-380, 1993.
Rosenfield et al., “Phototherapy effect on the incidence of patent ductus arteriosus in premature infants: prevention with chest shielding,” Pediatrics, 78: 10-14, 1986.
Travadi et al., “Patent ductus arteriosus in extremely preterm infants receiving phototherapy: does shielding the chest make a difference? A randomized, controlled trial,” Acta Paediatr, 95: 1418-1423, 2006.
Chest Shielding in Premature Infants During Phototherapy (SLIGHT), ClinicalTrials.gov, NCT02552927, https://clinicaltrials.gov/ct2/show/NCT02552927?term=NCT02555 . . . , accessed Sep. 20, 2021.
Bhola et al., “Chest shielding for prevention of a haemodynamically significant patent ductus arteriosus in preterm infants receiving phototherapy,” Cochrane Database Syst Rev., 3;(11):CD009816, 2015.
International Search Report and Written Opinion for PCT Patent Application No. PCT/US22/78763, mailed on Feb. 17, 2023, 14 pages.
International Preliminary Report on Patentability for International Application No. PCT/US2022/078763, entitled “Phototherapy Shield,” mailed on Apr. 30, 2024.

* cited by examiner

PHOTOTHERAPY SHIELD

BACKGROUND

A patent ductus arteriosus (PDA) is a common problem in premature infants with a reported incidence of 70% in premature infants≤29 weeks gestational age (GA). A persistent PDA has been associated with the development of neonatal morbidities such as pulmonary hemorrhage, bronchopulmonary dysplasia, intraventricular hemorrhage, necrotizing enterocolitis, and retinopathy of prematurity.

Current treatment options for PDA closure include the use of nonsteroidal inflammatory drugs (NSAIDs) and/or surgical ligation. Despite their effectiveness, NSAIDs have serious side effects including renal dysfunction, decrease in blood flow to the brain, platelet dysfunction, intestinal perforation, and necrotizing enterocolitis. Surgical PDA ligation has also been associated with serious complications such as bleeding, vocal cord paralysis, chylothorax, ligation of arterial structures within the chest, pneumothorax, and death. Due to the serious complications of the current treatments, alternative methods to prevent PDA related symptoms are urgently required.

One such alternative method is to target the relationship between phototherapy treatment of infants and vasodilation of the PDA. The photorelaxation or dilation of blood vessels with light of a certain wavelength (e.g., 420-460 nm) has been verified in many animal studies and clinical studies in premature infants. It has been suggested that phototherapy induced dilation of the PDA may be primarily seen in premature infants due to increased translucency of their premature skin. In addition, LED phototherapy units in use since 2007 provide increasingly higher irradiance in the range of 20 to 30 $\mu W/cm^2/nm$ (microwatts per square centimeter per nanometer). This is an alarming concern, since the current LED units may be associated with increased dilation and higher incidence of PDA in premature infants that are being born at extremely low birth weights and even earlier gestational ages.

SUMMARY

Phototherapy shields and associated methods are provided. Such phototherapy shields and methods are useful for shielding an infant undergoing phototherapy, and more particularly, for shielding the chest of a premature infant undergoing phototherapy to treat jaundice.

A phototherapy shield for an infant includes a shield body that is sized and shaped to extend around at least a portion of a torso of an infant. A fastener is attached to the shield body to secure the phototherapy shield around the torso of the infant. The shield body includes a reflective foil layer that is sandwiched between an upper fabric layer and a lower fabric layer and that is configured to block phototherapy light.

In general, phototherapy light can have a wavelength in a range of about 400 nanometers to about 500 nanometers. The fabric layers of the phototherapy shield can be configured to pass the phototherapy light without substantial attenuation. The fabric layers can include a biocompatible material, a nonwoven fabric material, an elastic fabric material, or combinations thereof.

The reflective foil layer of the phototherapy shield can have a transmittance of less than 0.1% of light having a wavelength in a range of about 400 nanometers to about 500 nanometers. An average thickness of the foil layer can be in a range of about 0.01 millimeters to about 0.1 millimeters.

The reflective foil layer can include metalized polymer film. For example, the foil layer can include aluminum.

The shield body of the phototherapy shield can be sized and shaped to cover a portion of the chest of the infant, e.g., a portion of the chest over the second to fourth thoracic rib position, to shield an area of skin above a patent ductus arteriosus (PDA). The shield body can be sized to cover an area that is at least 10% less than an expected total body surface area of the infant.

The expected total body surface area of the infant can be calculated based on other measurements such as height and weight. The Mosteller formula is one method that can be used to calculate body surface area (BSA), which takes the square root of the height (cm) multiplied by the weight (kg) divided by 3600, e.g., BSA ($m^2$)=square root of (height (cm)×weight (kg)/3600). The average BSA for a premature female is in the range of 0.07 $m^2$ to 0.12 $m^2$. The average BSA for a premature male is in the range of 0.06 $m^2$ to 0.12 $m^2$.

The shield body can have a length of about 20 centimeters to about 28 centimeters and a width of about 3 centimeters to about 5 centimeters. For example, the shield body can be rectangular and can have a length-to-width ratio of about 3.5:1 to about 4:1. The reflective foil layer can have a length of about 6 centimeters to about 8 centimeters and a width of about 2 centimeters to about 4 centimeters. For example, the reflective foil layer can have a length-to-width ratio of about 7:3.

A method of preparing an infant for phototherapy includes applying a phototherapy shield to an infant, the phototherapy shield including a shield body that includes a reflective foil layer sandwiched between two fabric layers. The phototherapy shield is then secured around the torso of the infant using a fastener attached to the shield body. Applying the phototherapy shield to the infant can include positioning the shield body in a horizontal fashion on a chest of the infant over the second to fourth thoracic rib position.

A method of making a phototherapy shield for an infant includes preparing a shield body sized and shaped to extend around at least a portion of a torso of an infant, the shield body including a reflective foil layer sandwiched between an upper fabric layer and a lower fabric layer, the reflective foil layer configured to block phototherapy light. The method further includes attaching a fastener to the shield body, the fastener configured to secure the phototherapy shield around the torso of the infant.

In the above described phototherapy shields and associated methods, the fastener can be an elastic fastener. Preferably, the fastener is made from material that is soft, breathable, and flexible.

The incidence of PDA is 70% in premature infants≤29 weeks GA and a majority of these infants will require phototherapy for the management of unconjugated hyperbilirubinemia (jaundice). These infants are at high risk of developing complications from a hemodynamically significant PDA due to the vasodilatory effects of phototherapy. Currently, shielding of the eyes and gonads prior to the start of phototherapy is part of standard of care in term and preterm infants. The approach described here is useful to establish placement of a chest shield in premature infants prior to the start of phototherapy as a part of standard of care as well. Thus, every premature infant who is ≤29 weeks GA or is ≤1000 grams at birth would have a chest shield placed prior to being treated with phototherapy. Currently, the rates of preterm birth rates in the U.S. are increasing and the average cost for each infant born≤29 weeks GA admitted to the NICU can range from US$200,000 and up. Thus, the use of the chest shield may not only decrease complications from a PDA but also decrease the cost of hospitalization in preterm infants.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1A:
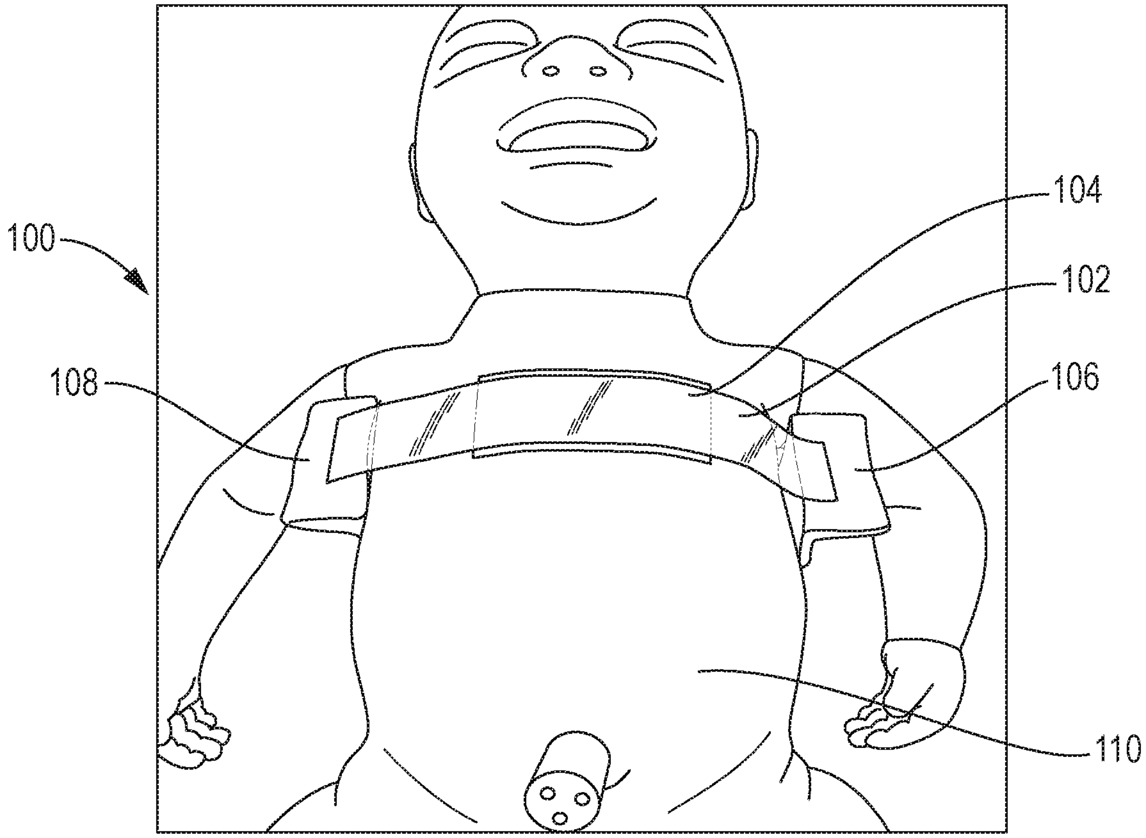
FIG. 1A (PRIOR ART)
FIGS. 1A and 1B are front and back views, respectively, of a prior phototherapy shield applied to an infant manikin.

A description of example embodiments follows.

Phototherapy treatment of neonatal jaundice includes exposing the afflicted infant to visible blue light having a wavelength in a range of 425-475 nm. During the phototherapy treatment of jaundiced infants, shields or shades are commonly placed over the eyes of the infant to protect the eyes from the blue light. Prior art eyeshades include self-adhesive shades that are affixed to the infant's temples and are kept in place with the use of a headband attached to the eyeshade by means of fabric fasteners such as VELCRO™ fasteners. Other eye shields include a strap of soft material, which is sized and shaped to pass around the head of the infant, and an eye pad that is attached to the strap. An example eye shield for protecting babies' eyesight during phototherapy treatment for neonatal jaundice is described in U.S. Pat. No. 6,973,930 B2.

Since light penetrates the translucent skin of premature infants, the present approach is based on the realization that chest shielding during phototherapy can prevent phototherapy induced dilation of the PDA. There are few clinical studies in premature infants that have evaluated the association between phototherapy used for jaundice and PDA. In an observational study, Barefield et al. reported increased incidence of PDA in infants with birth weights≤1000 grams undergoing phototherapy (Barefield E S, Dwyer M D, Cassudy G. Association of patent ductus arteriosus and phototherapy in infants weighing less than 1000 grams. *J Perinatal* 1993; 13: 376-380). They speculated that phototherapy induced dilation of the PDA may be primarily seen in premature infants due to increased translucency of their premature skin. There are only a few randomized clinical trials that have evaluated the effect of chest shielding during phototherapy on the incidence of PDA. The initial trial published in 1986 involved 72 infants and showed that chest shielding using aluminum foil during phototherapy reduced the incidence of PDA in 26-32 weeks GA infants by 50% (Rosenfield W, Sadhev S, Brunot V, Jhaveri R, Zabaleto I, Evans H E. Phototherapy effect on the incidence of patent ductus arteriosus in premature infants: prevention with chest shielding. *Pediatrics* 1986; 78: 10-14). The subsequent clinical trial published in 2006 involved 54 premature infants and failed to show any beneficial effect of chest shielding using aluminum foil during phototherapy on the incidence of PDA (Travadi J, Simmer K, Ramsay J, Doherty D, Hagan R. Patent ductus arteriosus in extremely preterm infants receiving phototherapy: does shielding the chest make a difference? A randomized, controlled trial. *Acta Paediatr* 2006; 95: 1418-1423). However, the lack of beneficial effect demonstrated in this study is likely due to inadequate power.

In addition, the randomized studies mentioned above were performed using standard phototherapy units which provided irradiance in the range of 4 to 12 $\mu W/cm^2/nm$. The LED phototherapy units in use since 2007 provide much higher irradiance in the range of 20 to 30 $\mu W/cm^2/nm$. Therefore, the current LED units may be associated with a much more enhanced photorelaxation effect and higher incidence of PDA specifically in very premature infants. A recently published study by Kapoor et al. did not show any benefits of a chest shield during phototherapy, but that study was also underpowered and enrolled more mature infants (Kapoor S, Mishra D, Chawla D, Jain S. Chest shielding in preterm neonates under phototherapy—a randomized control trial. *Eur. J Ped* 2021; 180:767-773). In addition, these previous randomized trials were not blinded. Due to the deficiencies present in these trials as well as the Cochrane paper on chest shielding (Bhola K, Foster J P, Osborn D A. Chest shielding for prevention of a haemodynamically significant patent ductus arteriosus in preterm infants receiving phototherapy. *Cochrane Database Syst Rev.* 2015 Nov. 3; (11):CD009816), another meta-analysis was performed by Mannan et al., which proposed that chest shielding during phototherapy may lead to a decrease in the incidence of PDA (Mannan J, Amin S. Meta-Analysis of the effect of chest shielding on preventing patent ductus arteriosus in premature infants. *Am J Perinatol* 2017; 34: 359-363).

Final analysis of a single center prospective double blind randomized pilot study (ClinicalTrials.gov, NCT02552927) reported a non-significant trend in increased incidence of symptomatic PDA, surgical ligation, necrotizing enterocolitis, chronic lung disease, and severe chronic lung disease at 36 weeks among non-shielded infants<27 weeks compared to infants in the chest shield group. In addition, this trial found no difference in the duration of phototherapy or peak total serum bilirubin levels between the two groups. These findings verify the association between phototherapy and incidence of PDA as well as verify the safety of a chest shield in preterm infants during phototherapy. The results of this trial are also similar to the results of the trial by Kim et al., who found an increased incidence of PDA in non-shielded preterm infants in comparison to infants who had a chest shield placed during phototherapy (Kim H S, Kim E K, Lee Y K, Lee H E, Park C H, Park R K. Influence of phototherapy on incidence of patent ductus arteriosus in very low birth weight infants. *J Korean Pediatr Soc.* 1997; 40: 1410-1418).

As stated above, four randomized trials to date have studied chest shielding during phototherapy to decrease the incidence of PDA in premature infants. These trials used a double folded piece of standard aluminum foil covered on one side by a gauze pad, which was taped to the infant's left chest as a shield. Described here is a chest shield made from a soft, elastic fabric with a reflective foil, e.g., an aluminized foil, embedded within the shield, e.g. embedded between fabric layers of the shield. The shield can be sized to wrap completely around the infant's chest. Preferably, this shield is adjustable for premature infants of varying size in order not to constrict chest rise. Although the top and bottom fabric layers are elastic and can be adjusted or stretched, shields of varying sizes may be used to ensure comfort and that the device is properly secured. For example, shields can come in three sizes, e.g., lengths, to fit different ranges of chest circumferences: small=20 cm-22 cm, medium=23 cm-25 cm, and large=26-28 cm. To the best of our knowledge, there have been no published data or trials using such a device or method to shield premature infants during phototherapy.

Advantageously, infants can have their chest shielded with the presently disclosed chest shield while undergoing phototherapy treatment. The chest shield is intended to be placed in a horizontal fashion on the chest over the second to fourth thoracic rib position to primarily shield the area of skin overlying the PDA. In certain embodiments, the shield combines one or more stretchable nonwoven biocompatible fabrics, such as Spunbond Polypropylene 100 gsm, K160082 60 gsm, K170081 35 gsm, and K170087 50 gsm fabrics (Uniquetex Engineered Nonwovens, Grover, NC, USA). The shield can be fashioned around the back and chest of the infant with the use of an elastic fastener, such as Avery Dennison Y9725D Wave C elastic diaper tape. Each shield includes a piece of reflective foil. Suitable reflective foils include foil DM146 and foil DE 050 (Dunmore, Bristol, PA, USA), which are aluminized polyester film (e.g., aluminized Mylar). The reflective foil can be adhered to the nonwoven fabric to shield the heart.

This shield design provides an improvement over shields used in prior clinical trials, which only utilized food grade aluminum that was taped to the skin of preterm infants during phototherapy. Except for a pilot trial at the University of Rochester conducted on chest shielding preterm infants during phototherapy (ClinicalTrials.gov, NCT02552927), none of the prior trials used a shield that wrapped around an infant's chest and back.

Figure 1B:
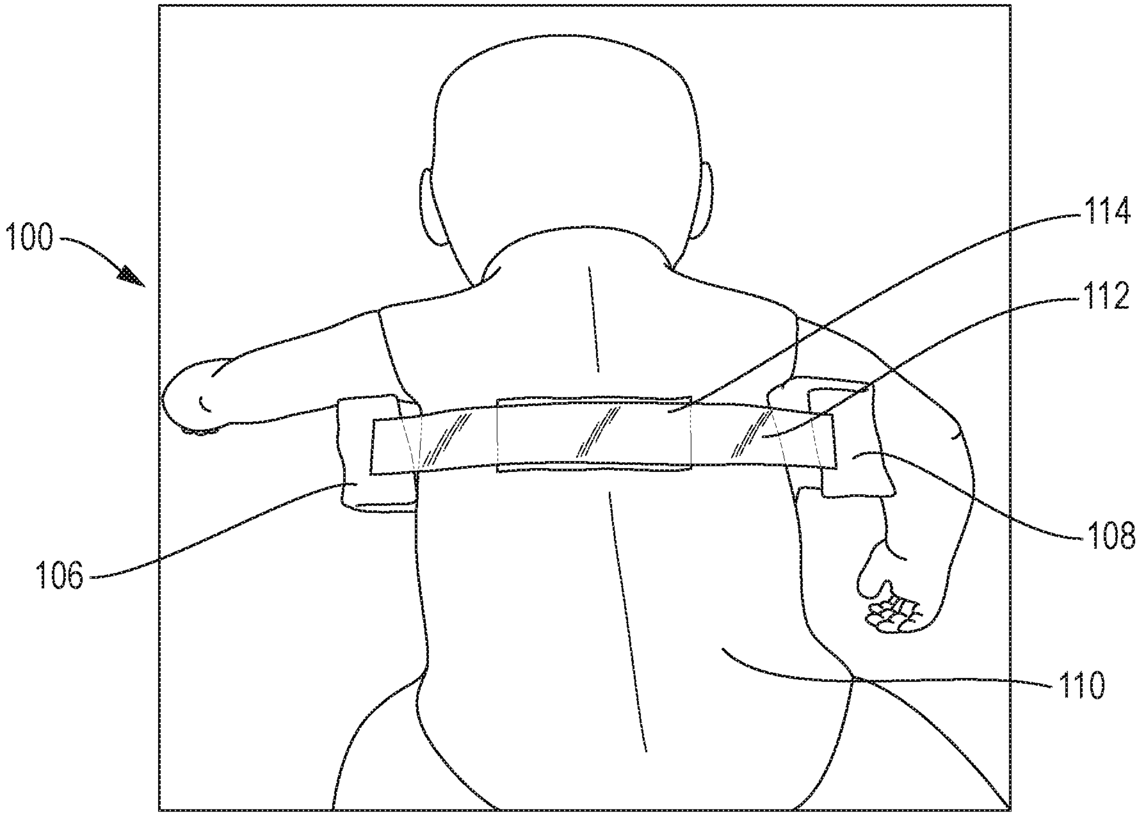
FIG. 1B (PRIOR ART)

An example of the shield used in the University of Rochester trial is shown in FIGS. 1A-1B. This trial also used food grade aluminum for the shield and, although it did not use tape to affix the shield to the infant's skin, it relied on VELCRO™ fasteners to keep the shield in the proper position. The concept of a chest shield for premature infants that would not need to be taped to the skin and that could easily be applied and wrapped around an infant, was developed during the design of the pilot trial. The shield used for the pilot study did not include the materials of the present shield and did not provide the ease of use of the present shield.

FIGS. 1A and 1B are front and back views, respectively, of the prior phototherapy shield device 100 applied to an infant manikin 110. The shield device 100 includes a front strap 102, a front shield region 104, a back strap 112, and a back shield region 114. Front and back straps 102 and 112 are connected by VELCRO™ fasteners 106 and 108. In one group of patients, the front shield region 104 included a food grade aluminum foil covered by a piece of paper. In the control group, no aluminum foil was present and the front shield region 104 included only the paper. Because the study was a double-blind study, the paper ensured that the presence of aluminum foil was hidden from the patient and the physician. The front and back of these shields were made from the same material. The straps were made from 3M™ Dual Lock™ Reclosable Fastener SJ3560.

Applying tape to the skin of premature infants has led to skin peeling and degradation of the skin, which has further increased the risk of sepsis and infection in these critically ill infants. In contrast, embodiments of the present shield use a fastener, e.g., Avery Dennison elastic tape, which is already in use in the diapers placed on these infants as standard of care. Using such a fastener ensures that the chest shield will not incur any injury or harm to the infant while remaining in place.

The aluminum foil used in the previous trials was only tested to assess if light could penetrate through the shield. The present shield material was tested using integrating spheres with Silicon (Si) detectors to measure the diffuse reflectance, total transmittance, and diffuse transmittance of the material, as further described in Example 1 below. The optical properties of the shield material were determined using the inverse Monte Carlo method. For thermal characterization of the shield, a Minco temperature sensor was utilized. These testing steps, which were not performed in the previous trials, help ensure the validity and safety of the shield device disclosed herein.

Figure 2A:
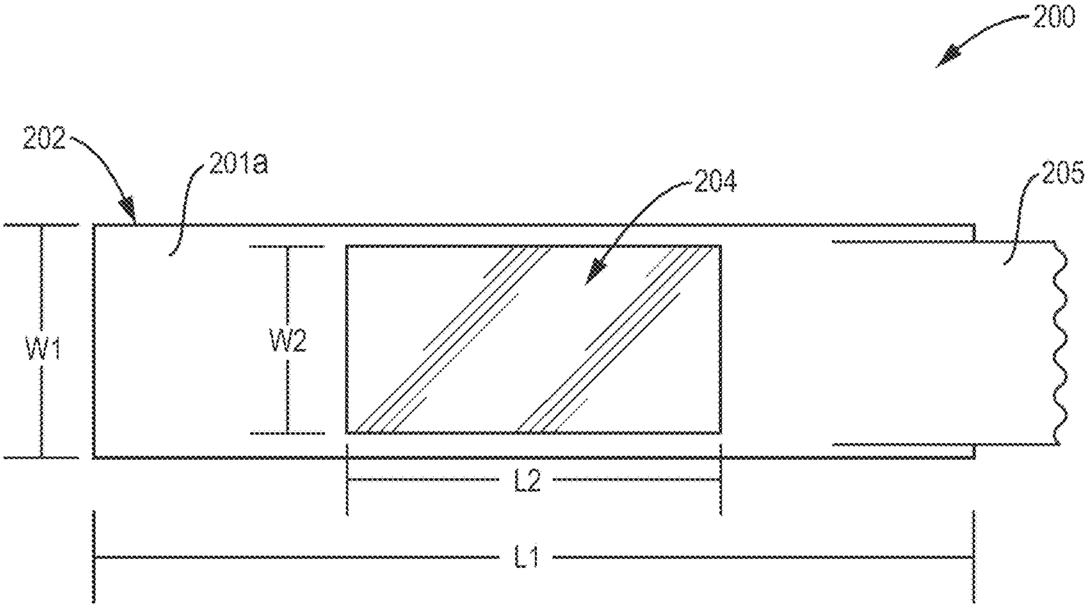
FIG. 2A is a schematic view of a phototherapy shield according to an example embodiment.
Figure 2B:
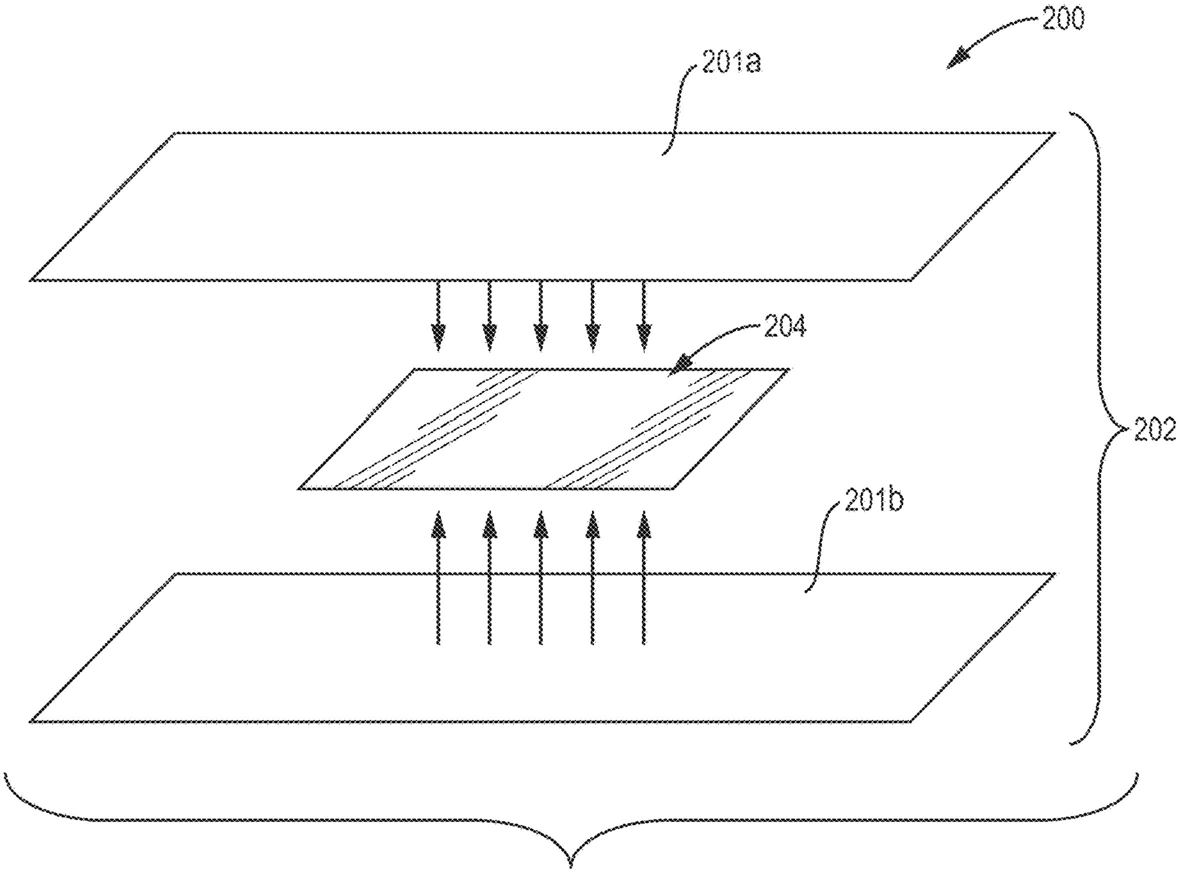
FIG. 2B is an exploded, sectional view of the shield of FIG. 2A illustrating the reflective foil sandwiched between fabric layers.

FIGS. 2A-2B schematically illustrate a phototherapy shield 200 according to an example embodiment. The phototherapy shield 200 includes a shield body 202 including fabric layers and a reflective foil layer 204 that is configured to block phototherapy light. The foil layer 204 is sandwiched between an upper (e.g., outer) fabric layer 201*a* and a lower (e.g., inner, patient facing) fabric layer 201*b*. The shield body 202 is sized and shaped to extend around at least a portion of a torso of an infant. At least one fastener 205 is attached to the shield body 202 to secure the phototherapy shield around the torso of the infant. In the example shown, the fastener 205 has one end that is attached to the shield body 202, at one end of the shield body. The other end of the fastener 205 is free but can be releasably attached to the other end of the shield body, to secure the shield to the infant.

As shown in FIG. 2A, the shield body 202 can have a length L1, which can be about 20 centimeters to about 28 centimeters, and a width W1, which can be about 3 centimeters to about 5 centimeters. For example, the shield body can have a length-to-width ratio of about 3.5:1 to about 4:1. In one example, the shield body 202 is rectangular, as illustrated in FIG. 2A, and has a length of about 24 centimeters and a width of about 4 centimeters. The reflective foil layer 204 can have a length, L2, of about 6 centimeters to about 8 centimeters and a width, W2, of about 2 centimeters to about 4 centimeters. For example, the reflective foil layer can have a length-to-width ratio of about 7:3. In one example, the reflective foil layer 204 is rectangular and has a length of about 7 centimeters and a width of about 3 centimeters.

Generally, the reflective foil layer 204 has a smaller width and length than the shield body, including the fabric layers 201*a* and 201*b*. As illustrated by the rows of up and down arrows in FIG. 2B, the reflective foil layer 204 can be bonded to one or both fabric layers 201*a*, 201*b*, to form the shield body 202. In that way, the reflective foil layer 204 forms a middle layer of the shield body. A suitable method of bonding the layers is heat bonding.

Advantageously, the fabric layers 201*a*, 201*a* can be configured to pass the phototherapy light without substantial attenuation. Further, the fabric layers can be made from a biocompatible material, which can be a nonwoven fabric material. Preferably, the fabric material is elastic, to facilitate applying the shield to the infant and to allow for chest expansion during breathing.

To effectively block phototherapy light, the reflective foil layer 204 can have a transmittance of less than 0.1% of light having a wavelength in a range of about 400 nanometers to about 500 nanometers. An average thickness of the foil layer can be in a range of about 0.01 millimeters to about 0.1 millimeters. As further described herein, the reflective foil layer 204 can be a metalized polymer film.

Figure 3A:
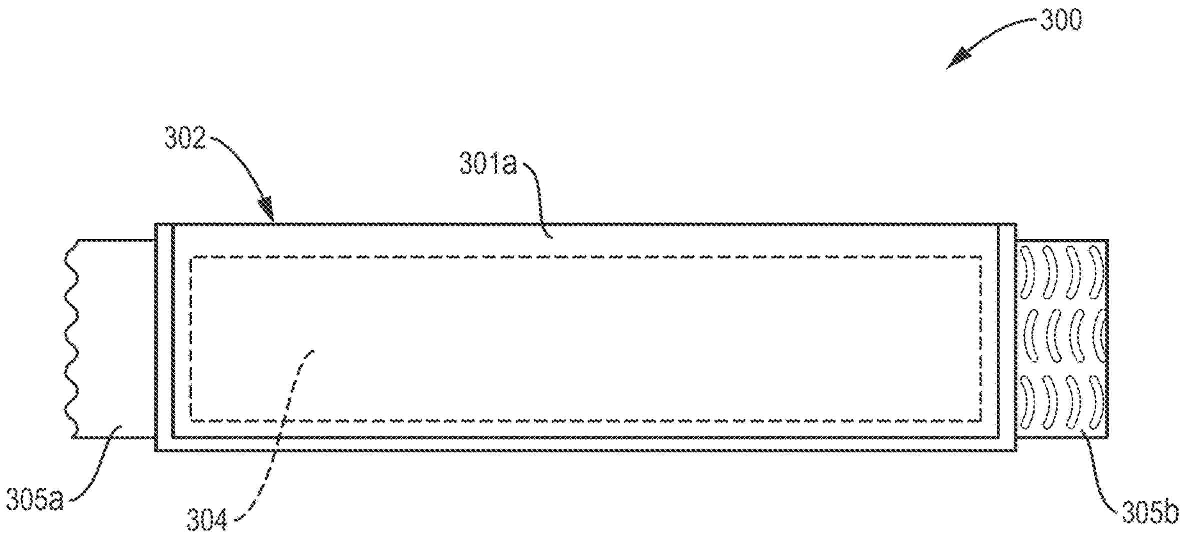
FIGS. 3A and 3B are front and back views, respectively, of a phototherapy shield according to an example embodiment.
Figure 3B:
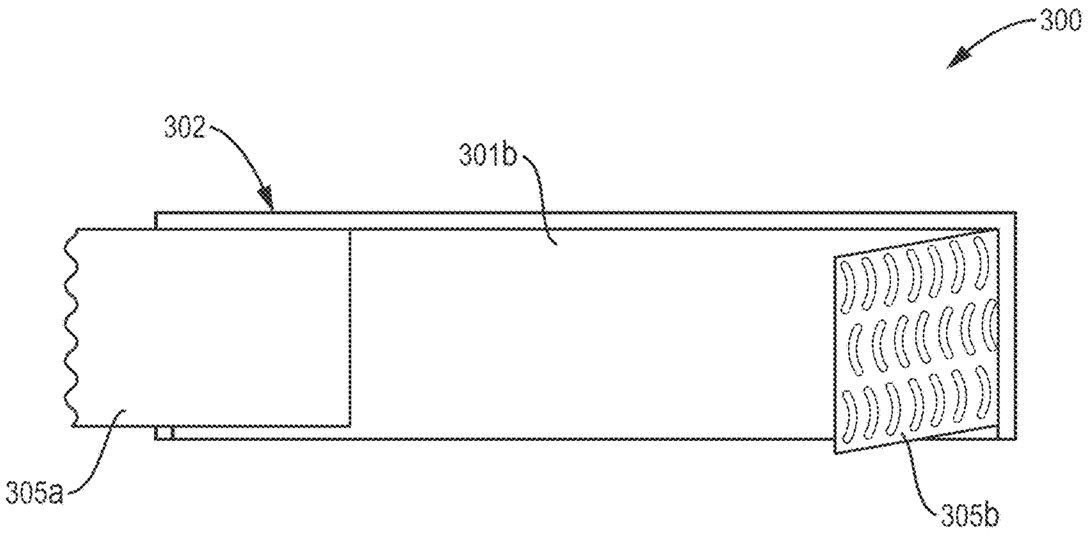
Figure 3C:
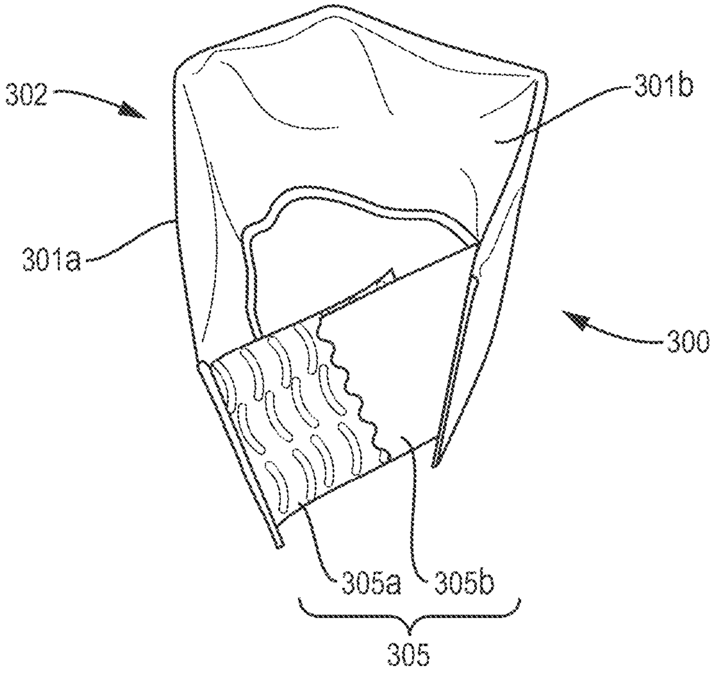
FIG. 3C is a perspective view of the shield of FIG. 3A in a closed loop configuration.

FIGS. 3A and 3B are front and back views, respectively, of a phototherapy shield 300 according to an example embodiment. Similar to phototherapy shield 200, the phototherapy shield 300 includes a shield body 302 including a reflective foil layer 304 that is sandwiched between an upper fabric layer 301*a* and a lower fabric layer 301*b*. The foil layer 304 is made from suitable material and configured to block phototherapy light. A fastener 305 is attached to the shield body 302 and can be used to secure the phototherapy shield 300 around the torso of the infant. As shown, the fastener 305 comprises two fastener parts 305*a*, 305*b*, each attached to one or the other end of the shield body 302. The fastener parts 305*a*, 305*b* can releasably attach to each other, to secure the shield to the infant. FIG. 3C is a perspective view of the shield 300 illustrating the shield in a closed loop configuration with fastener parts 305*a*, 305*b* attached to each other. The two fabric layers can be formed folding over one piece of fabric material. The sides opposite the fold can be bonded together, e.g. using heat bonding, to enclose the reflective foil layer.

Figure 4A:
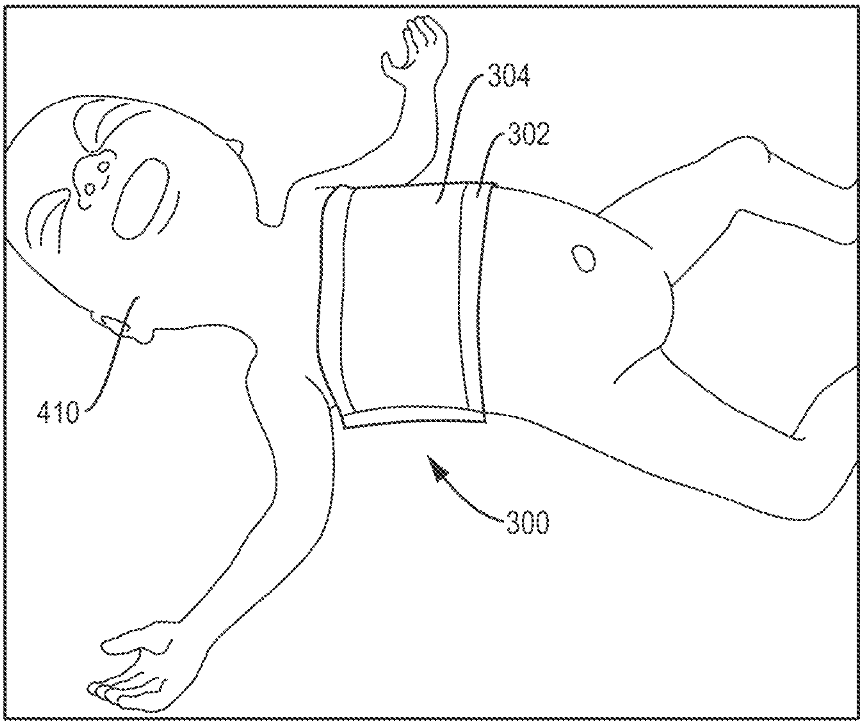
FIGS. 4A and 4B are front and back views, respectively, of the phototherapy shield of FIG. 3A illustrating the shield secured around the torso of an infant manikin.
Figure 4B:
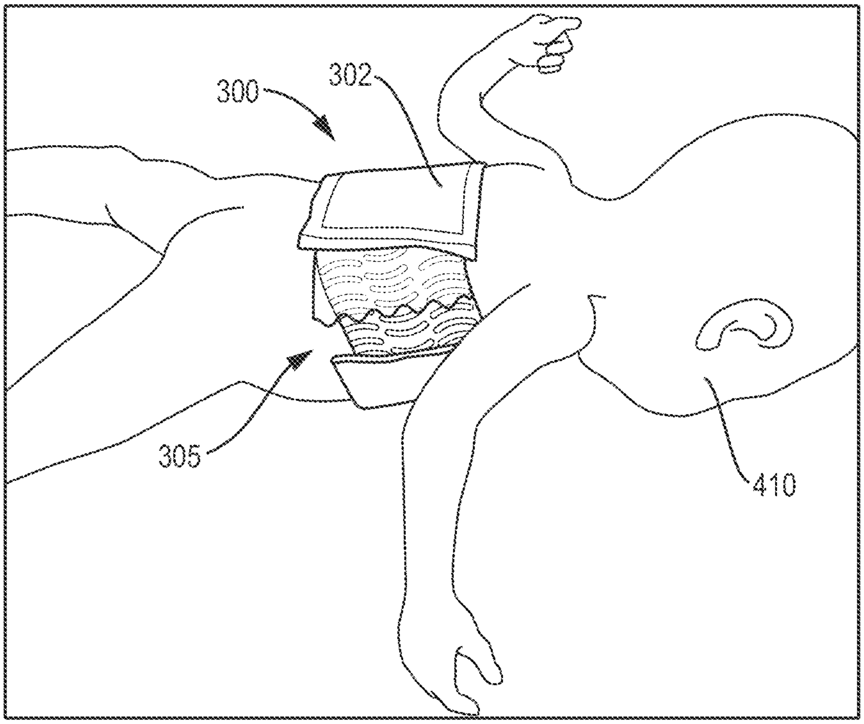

FIG. 4A is a front view of the phototherapy shield 300 of FIG. 3A, illustrating the shield secured around the torso of an infant manikin 410. The shield body 302 is sized and shaped to extend around at least a portion of a torso of the infant. The reflective foil layer 304 is positioned over the chest of the infant. FIG. 4B is back view of the shield 300 and infant manikin 410 illustrating the fastener 305, which securely attached the ends of the shield body 302 at a side of the infant manikin.

Figure 5A:
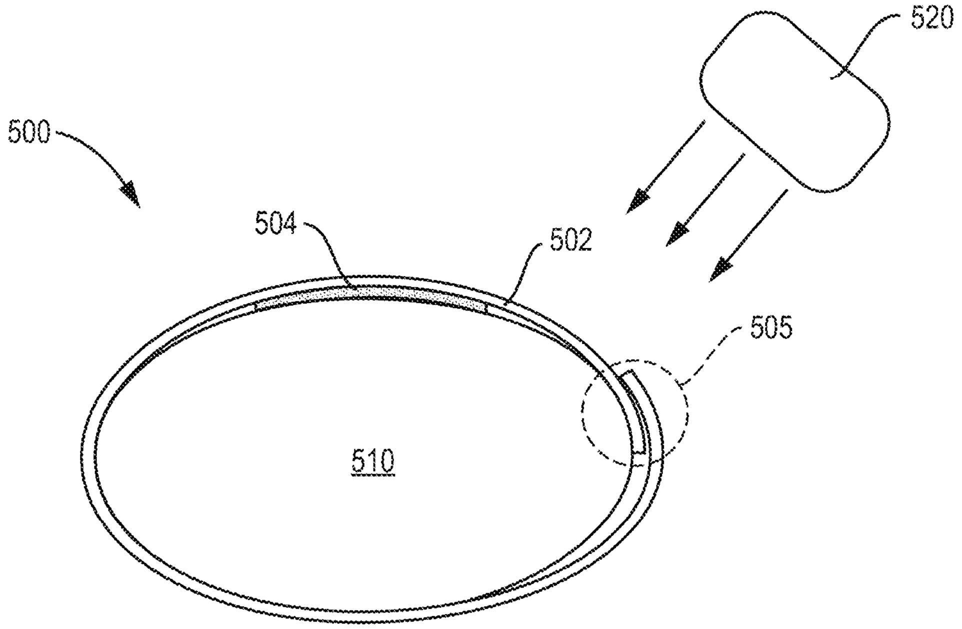
FIGS. 5A and 5B are schematic views illustrating example shields applied to an infant body during phototherapy.
Figure 5B:
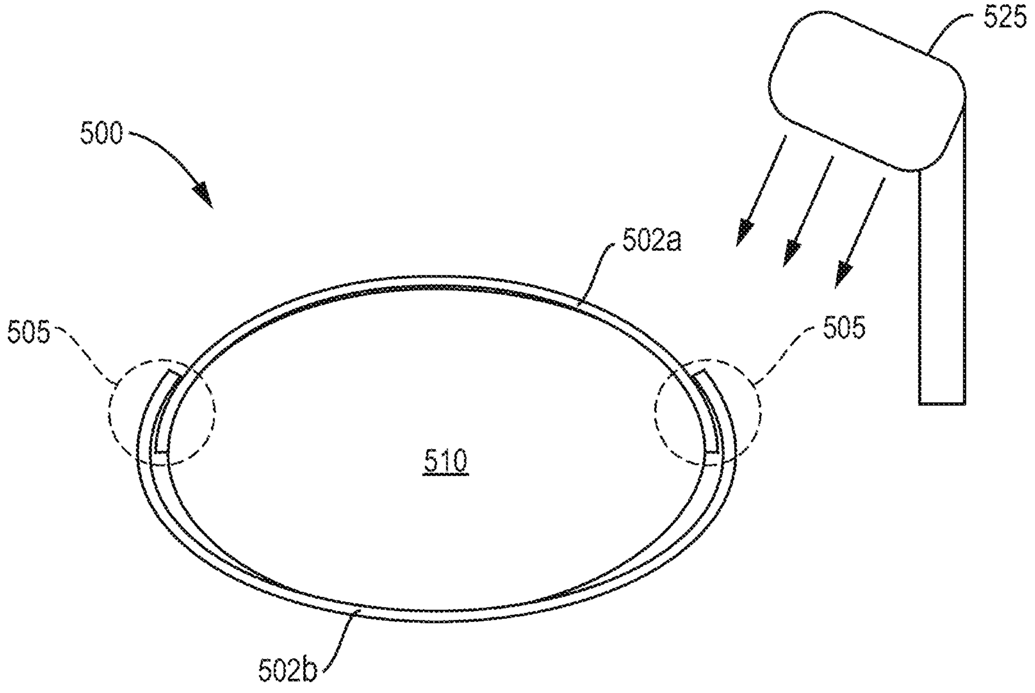

FIGS. 5A and 5B are schematic views illustrating example phototherapy shields applied to a biological body, such as the torso of an infant, during phototherapy. FIG. 5A illustrates a shield 500 that includes a shield body 502 which can be secured around biological body 510 by a fastener 505, to shield a selected portion of the body 510 from irradiation from phototherapy light source 520. The shield body includes a reflective foil 504, e.g., aluminized Mylar, as further described herein. In FIG. 5A, the reflective foil 504 is schematically illustrated below the shield body 502; however, the reflective foil is preferably sandwiched between layers of the shield body, as further described herein.

A shown in FIG. 5B, a shield 550 includes a two-part shield body comprising a front portion 502*a* and back portion 502*b*, which can be secured to each other and around the body 510 by fasteners 505. At least the front portion 502*a* of the shield body includes a reflective foil (not shown), as further described herein, to shield a selected portion of the body 510 from phototherapy light from light source 525. Light sources 520 and 525 are drawn differently to demonstrate different angles of illumination, e.g., phototherapy at an angle (FIG. 5A) and phototherapy more directly above the patient (FIG. 5B). Regardless of the angle, the phototherapy light sources and light intensity would typically be identical.

EXEMPLIFICATION

Example 1: Characterizing Materials for a Phototherapy Shield

Optimal shield properties and design are of vital importance for preventing adverse effects of light-based clinical procedures. The goal of this study was to select the most appropriate materials for a two-layer phototherapy shield. Four biocompatible fabrics, to be utilized as the layer contacting patient's skin, and two reflective materials, to be utilized as the layer facing the light source, were investigated. The optical properties of the four biocompatible fabrics and transmittance of the two reflective materials were determined in the 400-500 nm range. Absorption coefficient, scattering coefficient, and anisotropy factors of biocompatible fabrics were determined using integrating sphere spectrophotometry and an inverse Monte Carlo method. The materials that exhibited highest attenuation of the blue light were selected, a two-layer composite prototype was assembled and tested to ensure negligible temperature increase under clinically relevant exposure conditions. The testing protocol employed in this study may prove valuable for designing protective gear for a range of clinical procedures.

1. Introduction

Side effects from various phototherapy procedures have been well documented. Blue light phototherapy for treating jaundice in neonates has been shown to cause retinal damage as well as damage to red blood cells, which may lead to bronchopulmonary dysplasia, retinopathy, and necrotizing enterocolitis (Stokowski 2011). Blue light phototherapy has also been associated with the formation of patent ductus arteriosus (Stokowski 2011) and may increase the chance of melanocytic nevus development (Csoma et al. 2011). UV phototherapy for psoriasis, vitiligo, and polymorphic light eruption may lead to carcinogenesis, cataracts, lentigines, photoaging (Holme and Anstey 2004). Keratitis with facial erythema has also been reported forming after UV treatments (Komericki et al. 2005). Atrophy of the superonasal iris, iris transillumination defects, pigmentation on the anterior capsule, anisocoria, and dyscoria have all been reported developing in patients receiving Intense Pulsed Light (IPL) therapy (Javey et al. 2010) (Crabb et al. 2014). Therefore, it is important to use phototherapy shields to reduce side effects from light treatments (Stokowski 2011). Shielding must sufficiently attenuate treatment light to provide protection for the patient.

In this study, materials for a two-layered, blue light phototherapy shield were tested and compared. Reflective foils were considered for the top layer, facing the light source, while biocompatible fabrics were examined for the bottom layer, facing the patient. Biocompatible fabrics were evaluated using integrating sphere spectrophotometry. Reflective materials were characterized by transmittance measurements.

2.1 Biocompatible Fabrics

The optical properties of Spunbond Polypropylene 100 gsm, K160082 60 gsm, K170081 35 gsm, and K170087 50 gsm biocompatible fabrics (Uniquetex Engineered Nonwovens, Grover, NC, USA) were investigated using integrating sphere spectrophotometry. Seven samples were prepared for each material type. Lateral dimensions of the samples were at most 42×50 mm. Sample thicknesses ranged from 0.172±0.004–0.306±0.002 mm. Sample thickness was measured using a digital micrometer (293-340 Digital Micrometer, Mitutoyo, Japan).

2.2 Reflective Foils

Reflective foils DM146 and DE 050 (Dunmore, Bristol, PA, USA) were compared using transmittance spectrophotometry. Seven samples with lateral dimensions 45×12 mm were prepared for each foil. Average thicknesses of DM146 and DE 050 samples were 0.021±0.001 mm and 0.082±0.001 mm, respectively. Thicknesses were measured using a micrometer (293-340 Digital Micrometer, Mitutoyo, Japan).

2.3 Integrating Sphere Spectrophotometry

Figure 6:
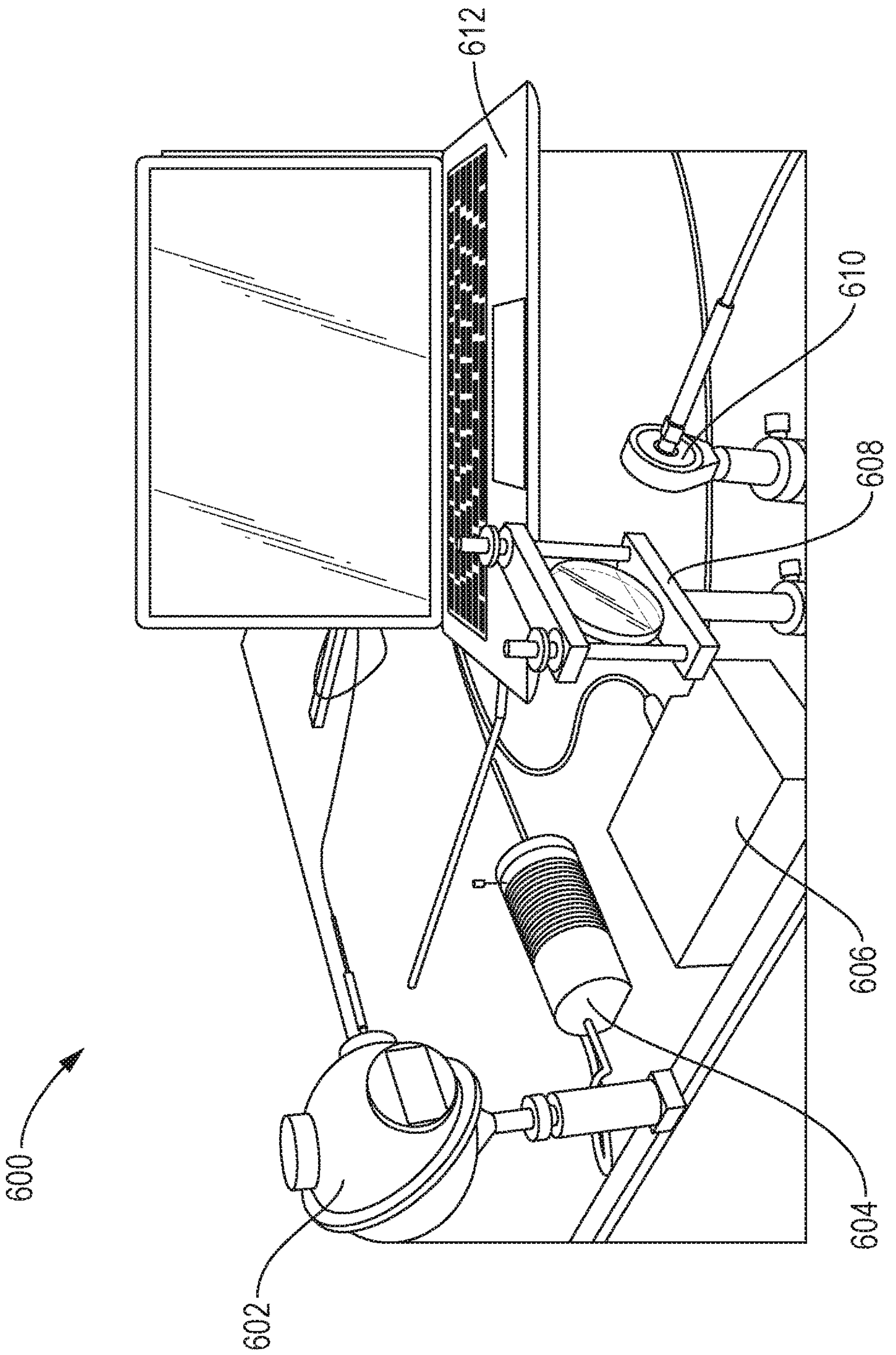
FIG. 6 illustrates an example integrating sphere set-up for measuring parameters to determine optical properties of sample shield material.

FIG. 6 illustrates a single integrating sphere system that was used to measure the total transmittance, diffuse transmittance, and diffuse reflectance of the biocompatible fabrics in the spectral range of 400-500 nm. The illustrated example set-up 600 includes an integrating sphere 602 and a halogen lamp 604 coupled into an optical fiber 610. Light emanating from the optical fiber was focused onto the sample by a lens 608. Light transmitted and reflected from the sample was collected by the integrating sphere 602 and detected by a grating spectrometer 606. Data acquisition was controlled by external PC 612. Samples were placed at the entrance and exit ports of the integrating sphere (4P-GPS-033-SL, Labsphere, North Sutton, N. H.) for transmittance and reflectance measurements, respectively. Light from a halogen lamp (HL-2000, 360-2000 nm, Ocean Optics, Dunedin, FL) was focused onto the samples. The focal spot had a diameter of 3 mm. Sample and exit ports of the integrating sphere had a diameter of 14 mm and 25.4 mm, respectively. Transmittance through air, and reflectance from Spectralon (>99% reflectance) were used as a reference. The exit port of the integrating sphere was opened during diffuse transmittance measurements to allow collimated light to escape. Collimated transmittance was calculated by subtracting diffuse transmittance from total transmittance at each wavelength investigated. An HR2000 spectrometer (Ocean Optics, Dunedin, FL) was coupled to the auxiliary port of the integrating sphere via an optical fiber (P600-2-SR, Ocean Optics, Dunedin, FL) to measure the spectral response in the 400-500 nm range.

2.4 Inverse Monte Carlo Technique

Absorption coefficients, scattering coefficients, and anisotropy factors of the biocompatible fabric materials were calculated from measured quantities under an assumption of Henyey-Greenstein scattering phase function (Henyey and Greenstein 1941) using an inverse hybrid Monte Carlo algorithm (Yaroslaysky et al. 1996). This method employed a forward Monte Carlo technique that accounted for the exact geometrical and optical properties of the integrating sphere walls and light losses at the edges of the samples. The forward Monte Carlo method was integrated into a Quasi-Newton inverse algorithm (Dennis and Schnabel 1983), optimized to reduce the number of forward Monte Carlo calls.

2.5 Transmittance Measurements

Transmittance through reflective materials in the spectral range of 400-500 nm was measured using a spectrophotometer (Lambda 1050, PerkinElmer Inc., Waltham, MA). The spectrophotometer slit width was set to 5 nm, and the wavelength step size was set to 2 nm. The illumination beam had a diameter of 4.5 mm. Transmittance through air was used as a reference. Transmittance of each reflective sample were measured twice, then averaged.

2.6 Temperature Monitoring

Figure 7:
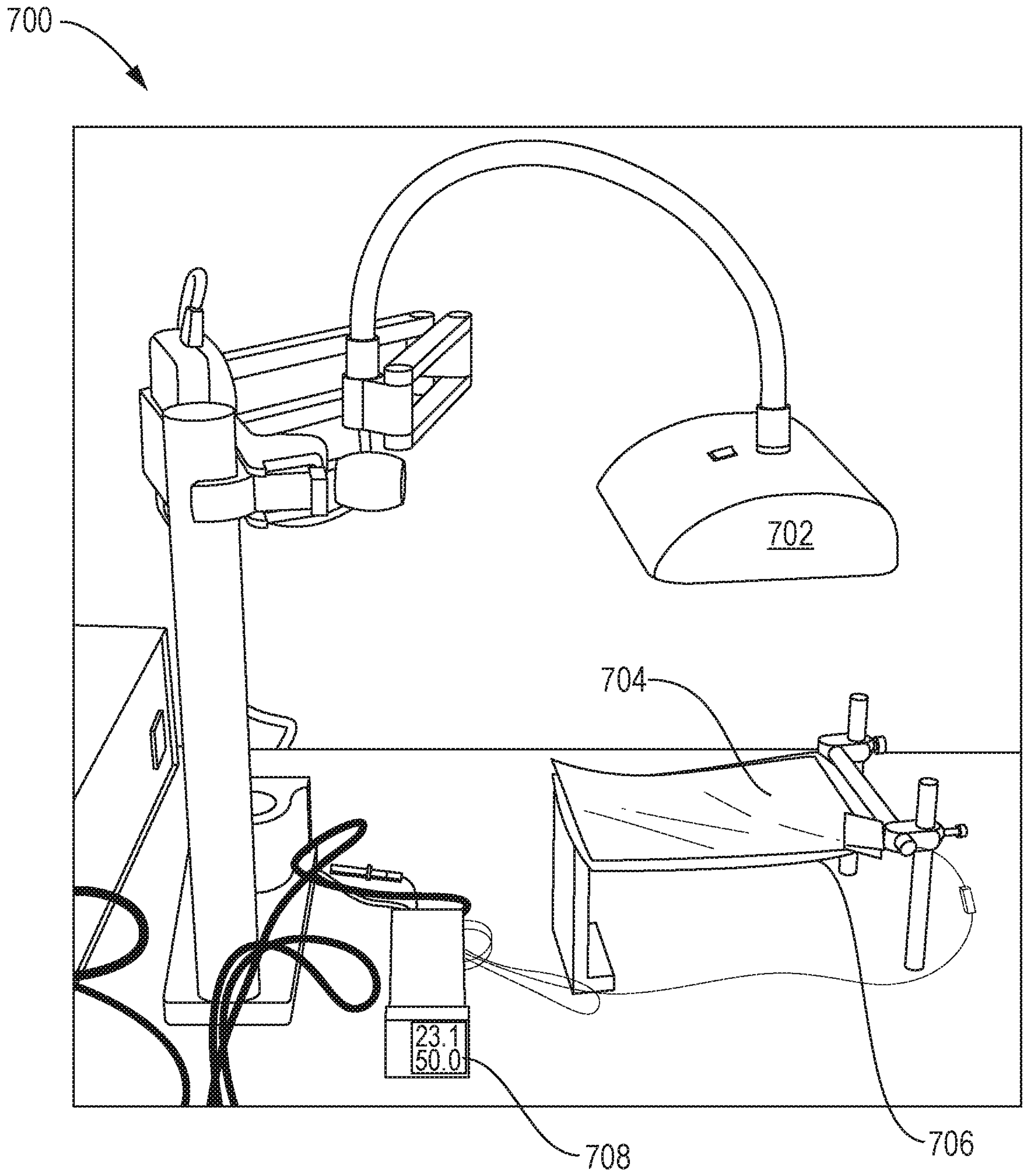
FIG. 7 illustrates an experimental setup used for shield material temperature monitoring.

After determining the optical properties and selecting appropriate biocompatible and reflective materials, a two-layer shield prototype was assembled. The temperature of the composite shield exposed to 450-470 nm light was monitored over a 48-hour time interval. The experimental arrangement used for monitoring the temperature of the shield is shown in FIG. 7. In the illustrated experimental setup 700 for shield material temperature monitoring, light from the phototherapy lamp 702 was incident onto the sample shield material 704. A temperature sensor 706 underneath the sample allowed the temperature monitor 708 to measure the temperature of the sample. A Natus neoBLUE mini LED phototherapy lamp (Natus Medical Incorporated, San Carlos, CA) was used as a light source. Shield samples were suspended above the optical table to provide thermal isolation. The lamp was placed 30.5 cm above the samples. The temperature sensor was attached to the biocompatible surface of the composite shield, where the shield would be in contact with patient skin. The sensor was connected to an external temperature monitor (CT16A2080-948, Minco, Minneapolis, MN). The geometry and duration of temperature monitoring experiments were exactly as those during the clinical phototherapy procedure.

3.1 Optical Properties of Biocompatible Fabric Materials

Figure 8A:
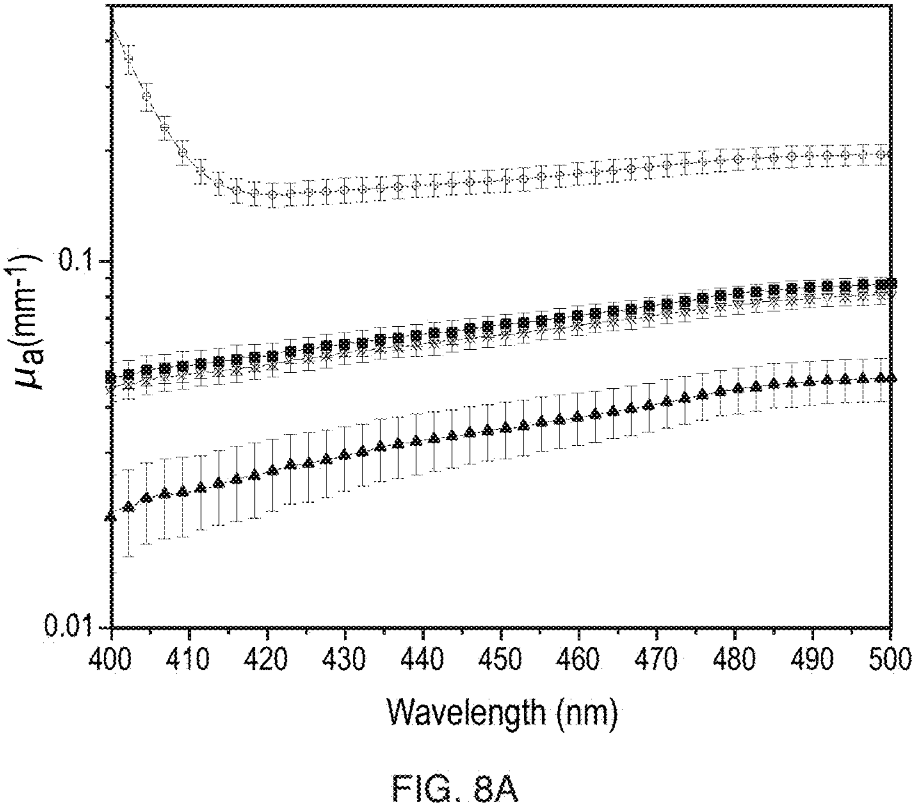
FIGS. 8A-8C are graphs illustrating absorption coefficients (FIG. 8A), scattering coefficients (FIG. 8B), and anisotropy factors (FIG. 8C) of biocompatible fabric materials at light wavelengths between 400-500 nm. Squares—Spunbond Polypropylene 100 gsm. Circles with a Cross—K160082 60 gsm. Half-filled Upright Triangle—K170081 35 gsm. Upside-down Triangle with an X—K170087 50 gsm. Bars—standard deviations.
Figure 8B:
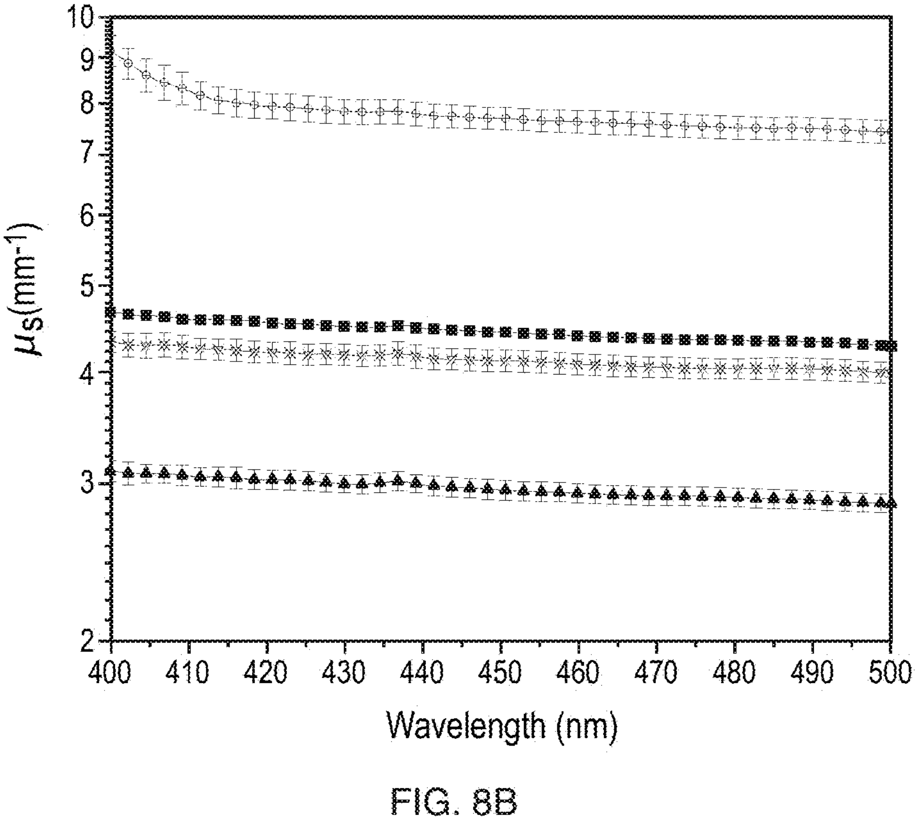
Figure 8C:
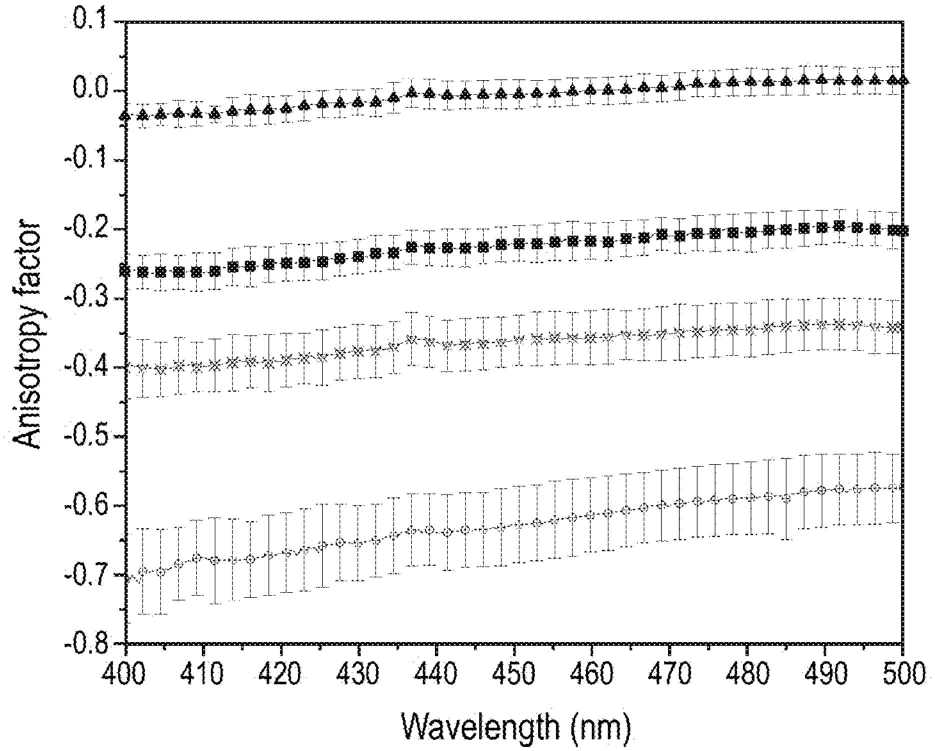

Absorption coefficients, scattering coefficients, and anisotropy factors of biocompatible fabric materials, determined in the spectral range of 400-500 nm, are shown in FIGS. 8A-8C. Absorption coefficients are presented in FIG. 8A. Absorption of Spunbond Polypropylene 100 gsm, K170081 35 gsm, and K170087 50 gsm monotonously increase with increasing wavelength. The absorption spectrum of K160082 60 gsm decreases with increasing wavelength between 400-420 nm, then increases with wavelength in the 420-500 nm range. K160082 60 gsm exhibited the greatest absorption out of all biocompatible fabrics investigated, ranging between 0.4 and 0.1 $mm^{-1}$ over the entire spectral range. The absorption of all other fabrics was less than 0.09 $mm^{-1}$.

Scattering coefficients are shown in FIG. 8B. Scattering of all fabrics decreased with increasing wavelength. K160082 60 gsm has the greatest scattering over the entire spectral region, with coefficients greater than 7.3 $mm^{-1}$. All other fabrics have scattering less than 4.6 $mm^{-1}$.

Anisotropy factors are presented in FIG. 8C. All fabrics exhibited increasing anisotropy with increasing wavelength. Anisotropy of Spunbond Polypropylene 100 gsm, K160082 60 gsm, and K170087 50 gsm are negative over the entire spectral range, whereas K170081 35 gsm has positive values between 458-500 nm. K160082 60 gsm has the greatest negative anisotropy factors ranging between −0.7 and −0.65 over the investigated spectral region.

Of the four biocompatible fabrics investigated, K160082 60 gsm has the greatest absorption and scattering in the 400-500 nm spectral range. The results show that scattering is the dominant attenuation process. Calculated absorption coefficients are an order of magnitude lower than the scattering coefficients. Due to the low absorption, a low temperature increase in the fabric during treatment can be expected. Moreover, K160082 60 gsm has the largest negative anisotropy factors out of the four fabrics tested. Thus, light has the highest probability of exhibiting backscattering when incident on fabric K160082 60 gsm. Due to predominant backscattering properties of the K160082 60 gsm fabric, more light will propagate towards the light source as compared to towards the patient. These results indicate that out of the four biocompatible fabrics tested, K160082 60 gsm is the most appropriate material for the bottom layer (e.g. the fabric layer) of the blue light phototherapy shield.

Ideally, the reflective material within the shield should predominately block the waves of blue light phototherapy and avoid any vasodilation. Thus, when undergoing phototherapy, infants should be placed on their backs or bellies and have the chest shield positioned in a such a manner to ensure that the reflective material is covering the upper left chest. Yet, infants may be positioned in a side lying position due to clinical necessity or the phototherapy light may have to be positioned at an angle rather than straight above. Although it is unlikely that an infant is placed in a position that the light is bypassing the reflective material, to ensure maximum protection, the chest shield design should preferably include a biocompatible fabric that provides some degree of blue light reduction although this would not be considered significant attenuation. Fabric K160082 60 was chosen since it exhibited these qualities to a higher degree in comparison to the other fabrics.

3.2 Transmittance Measurements of Reflective Materials

Transmittance of the two reflective materials were below 0.1% over the entire 400-500 nm range. Average transmittance measurements ranged between 0.039-0.071%, and 0.024-0.045% for foils Dm146 and DE 050, respectively. Lower transmittance points to higher attenuation of 400-500 nm light by foil DE 050 as compared to foil Dm146. Therefore, foil DE 050 was selected for the top layer of the blue light phototherapy shield.

3.3 Temperature Monitoring of Selected Shielding Materials

Based on the results of the optical experiments, composite shields were prepared with reflective foil DE 050 as the top layer facing the light and fabric K160082 60 gsm as the bottom layer facing patient's skin. Recorded shield temperatures ranged between 16.3° C. and 23.3° C. when exposed to blue treatment light. Temperatures of the shields followed the same temperature trends as room temperature. Thus, the phototherapy lamp did not have a significant effect on the shield temperature.

The 2-layer design was undertaken to assess direct exposure of the reflective foil to light and its effect on temperature. Since there was no effect, a 3-layer shield (with a top layer covering the reflective foil) should have similar results demonstrating that the shield is safe and does not exert heat.

4. Discussion

Many studies have been made to characterize and compare shielding materials. The most common approach is to measure optical transmission of the shields in the spectral range of interest. Chin et al. (1987) had investigated the transmission of 250-800 nm light through 12 potential eye shields using a spectrophotometer system. Robinson et al. (1991) measured the transmission of 300-750 nm light through three eye shield materials while placed in phototherapy units, to account for reflection from the therapy unit walls. Otman et al. (2010) determined the UV transmission of commercial sunglasses and contact lenses that were allowed to be worn by patients during treatments using a spectrophotometry system. Abdulla et al. (2010) measured UV transmission through potential shielding materials for genital protection from UVA, broad band UVB, and narrow band UVB illumination. This study explored a more general approach that can be utilized not only for testing and comparing prospective shields, but also to inform their selection, optimization, and design. Since attenuation of light is governed by the optical properties of the medium, this study started with determining the absorption coefficients, scattering coefficients, and anisotropy factors of the materials from diffuse reflectance and transmittance measurements using integrating sphere spectrophotometry (Jacques and Gaeeni 1989, Yaroslaysky et al. 2002, Bashkatov et al. 2005, Salomatina et al. 2006) and inverse Monte Carlo technique. This approach enables comparison of the shield attenuation properties irrespectively of the material thickness and allows for its optimization without exhaustive repetitive transmission measurements.

In conclusion, selecting shielding materials based on its optical and thermal properties enables straightforward optimization of shield design and ensures proper patient protection during phototherapy. While this study focused on shielding for blue light phototherapy, this method for characterizing shield materials can be utilized for any desired wavelength range and phototherapy procedure.

REFERENCES

Abdulla, F. R., Breneman, C., Adams, B., & Breneman, D. Standards for genital protection in phototherapy units. *Journal of the American Academy of Dermatology.* 62(2), 223-226, doi: 10.1016/j.jaad.2009.04.060 (2010).

Bashkatov, A. N., Genina, E. A., Kochubey V. I., & Tuchin V. V., Optical properties of human skin, subcutaneous and mucous tissues in the wavelength range from 400 to 2000 nm, *J. Phys. D: Appl. Phys.* 38 2543 (2005).

Chin, K. C., Moseley, M. J., & Bayliss, S. C. Light transmission of phototherapy eyeshields. *Archives of Disease in Childhood.* 62, 970-971 (1987).

Crabb, M., Chan, W. O., Taranath, D., & Huilgol S. C. Intense pulsed light therapy (IPL) induced iritis following treatment for a medial canthal capillary malformation. *Australiasian Journal of Dermatology.* 55, 289-291, doi: 10.1111/ajd.12137 (2014).

Csoma, Z., et al. Neonatal Blue Light Phototehrapy and Melanocytic Nevi: A Twin *Study. Pediatrics.* 128(4), e856-e864 (2011).

Dennis, J. E. & Schnabel, R. B. *Numerical Methods for Unconstrained Optimization and Nonlinear Equations* (Prentice-Hall, Upper Saddle River, 1983).

Henyey, L. G. & Greenstein, J. L. Diffuse radiation in the Galaxy. *Astrophys.* 1 93, 70-83 (1941).

Holme, S. A., & Anstey, A. V. Phototherapy and PUVA photochemotherapy in children. *Photodermatol Photoimmunol Photomed.* 20, 69-75 (2004).

Jacques, S. L., & Gaeeni, M. O., Thermically induced changes in optical properties of *heart, Images of the Twenty-First Century. Proceedings of the Annual International Engineering in Medicine and Biology Society,* 4, 1199-1200, doi: 10.1109/IEMBS.1989.96158 (1989).

Javey, G., Schwartz, S. G., & Albini, T. A. Ocular Complication of Intense Pulsed Light Therapy: Iris Photoablation. *Dermatol Surg.* 36, 1446-1468, doi: 10.1111/j.1524-4725.2010.01661.x (2010).

Komericki, P., Fellner, P., El-Shabrawi, Y., & Ardjomand, N. Keratopathy after ultraviolet B phototherapy. *Wien Klin Wochenschr.* 117(7-8), 300-302 (2005).

Otman, S. G. H., et al. Eye protection for ultraviolet B phototherapy and psoralen ultraviolet A patients. *Photodermatol Photoimmunol Photomed.* 26, 143-150 (2010).

Robinson, J., Moseley, M. J., Fielder, A. R., & Bayliss, S. C. Light transmission measurements and phototherapy eye-patches. *Archives of Disease in Childhood.* 66, 59-61 (1991).

Salomatina, E., Jiang, B., Novak, J. & Yaroslaysky, A. N. Optical properties of normal and cancerous human skin in the visible and near-infrared spectral range. *J. Biomed. Opt.* 11(6), 064026. https://doi.org/10.1117/1.2398928 (2006).

Skinner, M. G. et al. Changes in optical properties of ex vivo rat prostate due to heating. *Phys. Med. Biol.* 45, 1375-1386 (2000).

Stokowski, L. A. Fundamentals of Phototherapy for Neonatal Jaundice. *Advances in Neonatal Care.* 11(5S), S10-S21 (2011).

Yaroslaysky, A. N. et al. Optical properties of selected native and coagulated human brain tissues in vitro in the visible and near infrared spectral range. *Phys. Med. Biol.* 47(12), 2059-2073 (2002).

Yaroslaysky, I. V., Yaroslaysky, A. N., Goldbach, T. & Schwarzmaier, H. J. Inverse hybrid technique for determining the optical properties of turbid media from integrating-sphere measurements. *Appl. Opt.* 35(34), 6797-6809 (1996).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A phototherapy device for an infant, the device comprising:

a device body configured to be sized and shaped to extend around at least a portion of a torso of an infant, the device body sized to cover an area that consists of at least 50% less than an expected total body surface area of the infant, the device body comprising a shielding region surrounded by a non-shielding region, the device body including an upper fabric layer and a lower fabric layer, wherein the shielding region of the device body further includes a reflective foil layer sandwiched between the upper fabric layer and the lower fabric layer and defining the shielding region, the reflective foil layer configured to block phototherapy light and configured to shield a heart of the infant from the phototherapy light, the reflective foil layer consisting of a length of 6 centimeters to 8 centimeters and a width of 2 centimeters to 4 centimeters, and consisting of a smaller length and width than a length and width of the device body including the fabric layers, and the fabric layers configured to pass the phototherapy light without substantial attenuation; and a first fastener attached to a first end of the device body and configured to be releasably attached to a second end of the device body or to a second fastener attached to the second end of the device body, to secure the phototherapy device around the torso of the infant.

2. The phototherapy device of claim 1, wherein the device body has a length of 20 centimeters to 28 centimeters and a width of 3 centimeters to 5 centimeters.

3. The phototherapy device of claim 2, wherein the device body has a length-to-width ratio of 3.5:1 to 4:1.

4. The phototherapy device of claim 2, wherein the device body is rectangular.

5. The phototherapy device of claim 1, wherein the fabric layers comprise a biocompatible material.

6. The phototherapy device of claim 1, wherein the fabric layers comprise a nonwoven fabric material.

7. The phototherapy device of claim 1, wherein the fabric layers comprise an elastic fabric material.

8. The phototherapy device of claim 1, wherein the reflective foil layer has a transmittance of less than 0.1% of light having a wavelength in a range of 400 nanometers to 500 nanometers.

9. The phototherapy device of claim 1, wherein the reflective foil layer has an average thickness in a range of 0.01 millimeters to 0.1 millimeters.

10. The phototherapy device of claim 1, wherein the reflective foil layer comprises metalized polymer film.

11. The phototherapy device of claim 1, wherein the reflective foil layer comprises aluminum.

12. The phototherapy device of claim 1, wherein the phototherapy light has a wavelength in a range of 400 nanometers to 500 nanometers.

13. The phototherapy device of claim 1, wherein the device body is configured to be sized and shaped to cover a chest of the infant over a second to fourth thoracic rib position, configured to shield an area of skin above a patent ductus arteriosus (PDA).

14. The phototherapy device of claim 1, wherein the reflective foil layer has a length-to-width ratio of 7:3.

15. The phototherapy device of claim 1, wherein the phototherapy device is configured to secure a surface of the lower fabric layer to remain in contact with skin of the infant during use, thereby securing the reflective foil layer over an area of skin of the infant and protecting the area of skin from phototherapy light.

16. The phototherapy device of claim 1, wherein the device body is configured to be sized to cover an area that is at least 77% to 95% less than the expected total body surface area of the infant.

* * * * *